United States Patent [19]

Spreafico et al.

[11] Patent Number: 5,674,490
[45] Date of Patent: Oct. 7, 1997

[54] ANTIBIOTIC GE1655 COMPLEX AND ITS FACTORS A, B, AND C

[75] Inventors: Franco Maria Spreafico; Ernesto Riva; Graziella Beretta, all of Milan; Khalid Islam, Como; Maurizio Denaro, Opera, all of Italy

[73] Assignee: Gruppa Lepetit S.p.A., Varese, Italy

[21] Appl. No.: 456,010

[22] Filed: May 31, 1995

Related U.S. Application Data

[62] Division of Ser. No. 321,655, Oct. 11, 1994, abandoned, which is a continuation of Ser. No. 221,560, Mar. 31, 1994, abandoned, which is a continuation of Ser. No. 30,033, filed as PCT/EP91/01475, Aug. 5, 1991, published as WO92/04457, Mar. 19, 1992, abandoned.

[51] Int. Cl.⁶ .............................. A61K 35/74; C12P 17/12
[52] U.S. Cl. ............................................. 424/115; 435/119
[58] Field of Search ................................................ 424/115

[56] References Cited

PUBLICATIONS

Iwasaki et al, Chem. Pharm. Bull., 30(11): 4006–4014 (1982).

ARAI et al, J. Antib., 23 (2): 107–112 (Mar. 1970).

Primary Examiner—Jerome D. Goldberg
Attorney, Agent, or Firm—J. Michael Dixon

[57] ABSTRACT

The present invention is directed to a new antibiotic denominated antibiotic GE1655 complex, its factors antibiotic GE1655 factor A, antibiotic GE1655 factor B, and antibiotic GE1655 factor C, the pharmaceutical acceptable salts thereof, the pharmaceutical compositions thereof, and their use as medicaments against bacteria and fungi, particularly for the treatment of fungal infections in animals and human beings.

7 Claims, 4 Drawing Sheets

ANTIBIOTIC GE1655 COMPLEX AND ITS FACTORS A, B, AND C

CROSS-REFERENCE TO RELATED APPLICATION

This is a division of application Ser. No. 08/321,655, filed Oct. 11 1994, abandoned, which is a continuation of application Ser. No. 08/221,560, filed Mar. 31, 1994, now abandoned which is a continuation of Ser. No. 08/030,003, filed as PCT/EP91/01475 Aug. 5, 1991 published as WO92/04457 Mar. 19, 1992 now abandoned herein incorporated by reference.

The present invention concerns a new antibiotic substance arbitrarily denominated antibiotic GE1655 complex, its factors antibiotic GE1655 factor A, antibiotic GE1655 factor B, and antibiotic GE1655 factor C, a mixture of said factors in any proportion, pharmaceutical acceptable salts thereof, pharmaceutical compositions thereof, and the use of these new antibiotic substances as medicaments, particularly for the treatment of fungal infections in animals and human beings. They can be also used for controlling phytopathogenic microorganisms in plants.

Another object of the present invention is a process for preparing antibiotic GE1655 complex and its factors A, B, and C which consists in culturing the new strain *Streptomyces hygroscopicus* ATCC 55085 or an antibiotic GE1655 producing variant or mutant thereof, recovering the complex from the fermentation broths, and separating the factors A, B, and C.

According to their physico-chemical properties antibiotic GE1655 complex and its factors A, B, and C can be assigned to the azalomycin class. Azalomycin, the most representative antibiotic of this class, is a macrocyclic polyhydroxyl lactone type antibiotic produced by *Streptomyces hygroscopicus* var. *zalomyceticus* as a mixture of at least three major components differing from each other in the substituents present on the nitrogens of the guanidino group (see U.S. Pat. No. 3,076,746 for the production of complex, J. Antib., Ser. A, 23, 107 (1970) for the isolation of the factors, and Chem. Pharm. Bull., 30, 4006 (1982) for the structure elucidation).

Other members of this class of antibiotics are, for example, guanidylfungin (Japan patent N. 83170482 and J. Antib., Ser. A, 37, 1161, 1170 (1984)), and copiamycin (U.S. Pat. No. 3,627,880).

*Streptomyces hygroscopicus* ATCC 55085 was isolated from a soil sample collected in Dehradun (India) and deposited on Aug. 6, 1990 with the American Type Culture Collection (ATCC), 12301 Parklawn Drive, Rockville, Md. 20852 Maryland, U.S.A., under the provisions of the Budapest Treaty.

The strain has been accorded accession number ATCC 55085.

The production of the antibiotic GE1655 complex is achieved by cultivating a streptomyces strain capable of producing it, i.e. *Streptomyces hygroscopicus* ATCC 55085 or an antibiotic GE1655 producing variant or mutant thereof, under aerobic conditions in an aqueous nutrient medium containing assimilable sources of carbon, nitrogen, and inorganic salts. Many of the nutrient media usually employed in the fermentation art can be used, however certain media are preferred.

Preferred carbon sources are glucose, mannose, galactose, starch, corn meal and the like. Preferred nitrogen sources are ammonia, nitrates, soybean meal, peptone, meat extract, yeast extract, tryptone, aminoacids, and the like. Among the inorganic salts which can be incorporated in the culture media there are the customary soluble salts capable of yielding sodium, potassium, iron, zinc, cobalt, magnesium, calcium, ammonium, chloride, carbonate, sulphate, phosphate, nitrate and the like ions.

Ordinarily, the antibiotic producing strain is pre-cultured in a shake flask, then the culture is used to inoculate jar fermentors for the production of substantial quantities of the antibiotic substances. The medium used for the pre-culture can be the same as that employed for larger fermentations, but other media can also be employed.

The antibiotic GE1655 producing strain can be grown at temperatures between 20° and 40° C., preferably between 24° and 35° C.

During the fermentation, the antibiotic production can be monitored by testing broth samples for antibiotic activity, for instance, by bioassay or TLC or HPLC procedures.

Sensitive organisms to the antibiotic GE1655 such as *Candida albicans* can be used as test organisms. The bioassay is conveniently performed by the agar diffusion method on agar plates. Maximum production of antibiotic activity generally occurs between the second and fifth day of fermentation.

Antibiotic GE1655 complex is produced by cultivating the strain *Streptomyces hygroscopicus* ATCC 55085, or an antibiotic GE1655 producing mutant or variant thereof, and it is mainly found in the culture broths.

In the present disclosure when dealing with the compounds of the invention in relation to their physico-chemical or biological properties, the term "antibiotic GE1655" is generally considered to refer to antibiotic GE1655 complex as recovered at the end of the fermentation process (see Example 2).

Morphological characteristics of *Streptomyces hygroscopicus* ATCC 55085

*Streptomyces hygroscopicus* ATCC 55085 grows well on most standard media. The vegetative mycelium, which has generally a thick and crusty surface, is composed of flexuous and branched hyphae with a diameter of about 0.8 micrometer. It exhibits a light cream to straw yellow color on most media. The aerial mycelium is composed of long and branched hyphae with a diameter of 0.8 to 1.0 micrometer and forms sporophores arranged in very closed and short spirals from 2 to 5 turns, which are situated as dense clusters on the main stems of the aerial hyphae. The aerial mycelium which in other actinomycetes is generally very hydrophobic, on certain media (ISP N.3, N.4, N.7, oatmeal, Czapeck glucose agar and ISP N.8 agar, with the addition respectively of: mannitol, galactose, lactose, mannose, dextrose, inositol, fructose, ramnose, and ribose) becomes moistened and exhibits dark and glistening patches which, with the age, spread all over the surface. The spores are round to slightly oval with a diameter of 1–1.2×1.6 micrometer. Their color is ash grey but when wetted it becomes dark brown to almost black.

Cultural characteristics of *Streptomyces hygroscopicus* ATCC 55085

For the examination of the cultural characteristics, *Streptomyces hygroscopicus* ATCC 55085 was cultivated on various standard media suggested by Shirling and Gottlieb (Shirling E. B. and Gottlieb D., 1966—Method for Characterization of Streptomyces Species Int. J. Syst. Bacteriol., 16, 313–340) with the addition of several media recommended by Waksman (Waksman, S. A. 1961—The Actinomycetes—The William and Wilkins Co. Baltimore; Vol. 2, 328, 334).

Color determination was made, when necessary, by the method of Maerz and Paul (A. Maerz and M. Rea Paul, 1950—A Dictionary of Color—2nd Edition McGraw-Hill Book Company Inc. New York). The ability of the organism to utilize different carbon sources was investigated by the method described by Shirling and Gottlieb. The cultural and physiological characteristics and the carbon sources utilization are reported in Tables I, II, and III.

The readings in Table I were taken after two weeks of incubation at 28° C.

TABLE I

Cultrual characteristics of strain
*Streptomyces hygroscopicus* ATCC 55085

| Culture media | Morphological Characteristics |
|---|---|
| ISP 2 (yeast extract malt agar) | Abundant growth with thick and crusty surface, light cream (10-C-3) with light brown reverse (12-I-10). Abundant formation of whitish aerial mycelium. Moderate formation of light grey, spores. |
| ISP 3 (oatmeal agar 20%) | Abundant growth with smooth surface, light cream (10-C-3). Abundant formation of ash grey spores. |
| Oatmeal agar 60% | Abundant growth with smooth surface, light cream (10-C-3). Moderate formation of light grey spores. |
| ISP 4 (inorganic salts-starch agar) | Moderate growth with smooth surface, straw yellow (10-F-2). Abundant formation of ash grey spores. |
| ISP 5 (glycerol-asparagine agar) | Moderate growth with thick and, slightly crusty surface, light yellow (10-F-3). Moderate formation of whitish aerial mycelium. |
| ISP 6 (peptone-yeast extract agar) | Moderate growth with slightly wrinkled surface, iron colorless. |
| ISP 7 (tyrosine agar) | Abundant growth with thick and wrinkled surface, brown with dark brown reverse. Deep brown with a reddish tinge melanine pigment (8-H-12). Abundant formation of light grey spores. |
| Hichey and Tresner's agar | Abundant growth with slightly. crusty surface, light cream (10-C-3) with deep amber reverse (12-F-9). Abundant formation of ash and grey spores. |
| Czapeck glucose agar | Moderate growth with smooth and thin surface colorless with lemon yellow edges. Moderate formation of light grey spores. |
| Glucose asparagine agar | Abundant growth with smooth and thin surface straw yellow (10-F-2). Moderate formation of light grey spores. |
| Nutrient agar | Moderate growth with smooth surface, colorless. Moderate white aereal mycelium |
| Potato glucose agar | Abundant growth with thick and slightly crusty surface, light brown. Abundant formation of light grey spores. |
| Calcium malate agar | Good growth with smooth surface, colorless with yellowish reverse. Moderate formation of white aereal mycelium. |

TABLE I-continued

Cultrual characteristics of strain
*Streptomyces hygroscopicus* ATCC 55085

| Culture media | Morphological Characteristics |
|---|---|
| Dextrose triptone agar | Abundant growth with slightly wrinkled surface, straw yellow (10-F-2) with deep golden reverse (10-G-7). Moderate formation of white aereal mycelium. |
| Egg albumine agar | Moderate growth with smooth and thin surface colorless with lemon yellow edges. Moderate formation of ash grey spores. |

Letter and numbers refer to the color determination according to Maerz and Paul (see above)

TABLE II

Physiological characteristics of
*Streptomyces hygroscopicus* ATCC 55085

| Tests | Results |
|---|---|
| Starch hydrolysis | positive (strong) |
| $H_2S$ formation | negative on medium n. 6, positive with lead acetate-strips |
| Tyrosine hydrolysis | positive (strong) |
| Caseine hydrolysis | positive (weak) |
| Gelatine liquefaction | positive (weak) |
| Calcium malate hydrolysis | positive (strong) |
| Litmus milk coagulation | negative |
| Litmus milk peptonization | positive |
| Nitrate reduction | positive (strong) |
| Melanine production | positive (strong) |

TABLE III

Carbohydrate utilization

| Carbon source | Growth |
|---|---|
| Arabinose | +++ |
| Dextrose | +++ |
| Fructose | +++ |
| Galactose | +++ |
| Mannose | +++ |
| Ramnose | +++ |
| Ribose | +++ |
| Xylose | +++ |
| Lactose | +++ |
| Maltose | +++ |
| Sucrose | +++ |
| Raffinose | +++ |
| Inositol | +++ |
| Mannitol | +++ |
| Cellulose | − |
| Salicin | + |

+++ abundant growth
+ moderate growth
− no growth
For this test medium ISP 8 (T. G. Pridham, D. Gottlieb J. Bacteriol., 56, 107–114, 1948) is used and the results are evaluated after 2 weeks of incubation at 28°–30° C.

CHEMOTAXONOMICAL CHARACTERISTICS

Cell wall analysis

The analysis of aminoacids present in the cell wall was carried out by the HPLC method described by M. Zanol and L. Gastaldo "HPLC Separation of the Three Stereoisomers of Diaminopimelic Acid in Hydrolyzed Bacterial Cells" XIV International Symposium on Column Liquid Chromatography, Boston U.S.A. 1990.

Whole cell sugar pattern

The analysis of the sugar content in the whole cell was carried out after hydrolysis of the freeze-dried biomass in 0.5N HCl at 170° C. for 70 min. in autoclave.

The resultant cell suspension was passed through a 0.77 micron Millipore filter, sugars were then derivatized using the method published by H. N. Englyst and J. H. Cummings: Analyst, 109, p.937–942 (1984).

Identity of *Streptomyces hygroscopicus* ATCC 55085

The strain producing antibiotic GE1655 was assigned to the genus streptomyces and classified as *Streptomyces hygroscopicus* because of the following chemical and morphological characteristics:

a) The presence of L,L-diaminopimelic acid in the cell wall b) The absence of diagnostic sugars in the whole cell hydrolyzate c) The differentiation of the aereal mycelium in chains of spores arranged in short and very closed spirals d) The presence on the aereal mycelium of black, glistening and moistened spots due to high hygroscopicity of the spores.

As with other microorganisms, the characteristics of antibiotic GE1655 producing strains are subject to variation. For example, artificial variants and mutants of the strain can be obtained by treatment with various known mutagens, such as U.V. rays, X-rays, high frequency waves, radioactives rays, and chemicals such as nitrous acid, N-methyl-N'-nitro-N-nitrosoguanidine, and many others. All natural and artificial variants and mutants which belong to a species of the genus *Streptomyces hygroscopicus* and produce antibiotic GE1655 are deemed equivalent to strain *Streptomyces hygroscopicus* ATCC 55085 for the purpose of this invention and are contemplated to be within the scope of this invention.

As mentioned above, antibiotic GE1655 complex is generally found mainly in the fermentation broths. The recovery of antibiotic GE1655 complex from the fermentation broths of the producing microorganism is conducted according to known per se techniques which include extraction with solvents, precipitation by adding non-solvents or by changing the pH of the solution, partition chromatography, reverse phase partition chromatography, ion-exchange chromatography, affinity chromatography, and the like.

A procedure for recovering the antibiotic of the invention from the fermentation broths include extraction with a water-immiscible organic solvent of the antibiotic or of its salts with counter ions designed to form ion pair soluble in organic solvent, followed by precipitation from the concentrated extracts possibly by adding a precipitating agent or further extraction of an aqueous residue thereof with a water-immiscible solvent.

The term "water-immiscible solvent", as used in this application, is intended to have the meaning currently given in the art to this term and refers to solvents that, at the conditions of use, are slightly miscible or pratically immiscible with water in a reasonably wide concentration range, suitable for the intended use.

Examples of water-immiscible organic solvents that can be used in the extraction of the antibiotic of the invention from the fermentation broths are: alkanols of at least four carbon atoms which may be linear, branched or cyclic such as n-butanol, 1-pentanol, 2-pentanol, 3-pentanol, 1-hexanol, 2-hexanol, 3-hexanol, 3,3-dimethyl-1-butanol, 4-methyl-1-pentanol, 3-methyl-1-pentanol, 2,2-dimethyl-3-pentanol, 2,4-dimethyl-3-pentanol, 4,4-dimethyl-2-pentanol, 5-methyl-2-hexanol, 1-heptanol, 2-heptanol, 5-methyl-1-hexanol, 2-ethyl-1-hexanol, 2-methyl-3-hexanol, 1-octanol, 2-octanol, cyclopentanol, 2-cyclopentylethanol, 3-cyclopentyl-1-propanol, cyclohexanol, cycloheptanol, cyclooctanol, 2,3-dimethyicyclohexanol, 4-ethylcyclohexanol, cyclooctylmethanol, 6-methyl-5-hepten-2-ol, 1-nonanol, 2-nonanol, 1-decanol, 2-decanol, and 3-decanol; ketones of at least five carbon atoms such as methyl isopropyl ketone, methyl propyl ketone, methyl isobutyl ketone, methyl n-amyl ketone, methyl isoamyl ketone and mixtures or functional derivatives thereof.

As known in the art, phase separation may be improved by salting the aqueous phase.

When, following an extraction, an organic phase is recovered containing a substantial amount of water, it may be convenient to azeotropically distill water from it. Generally, this requires adding a solvent capable of forming minimum azeotropic mixtures with water, followed by the addition of a precipitating agent to precipitate the desired product, if necessary. Representative examples of organic solvents capable of forming minimum azeotropic mixtures with water are: n-butanol, benzene, toluene, butyl ether, carbon tetrachloride, chloroform, cyclohexane, 2,5-dimethylfurane, hexane, and m-xylene; the preferred solvent being n-butanol.

Examples of precipitating agents are petroleum ether, lower alkyl ethers, such as ethyl ether, propyl ether, and butyl ether, and lower alkyl ketones such as acetone.

According to a preferred procedure for recovering antibiotic GE1655 complex, the filtered fermentation broths can be contacted with an adsorption matrix followed by elution with a buffered polar water-miscible solvent or a mixture thereof, concentration under reduced pressure, extraction with water-immiscible solvents, and precipitation with a precipitating agent of the type already mentioned above.

Examples of adsorption matrixes that can be conveniently used in the recovery of the antibiotic substance of the invention, are polystyrene or mixed polystyrene-divinylbenzene resins such as S112 (Dow Chemical Co.), Amberlite XAD2 or XAD4 (Rohm and Haas), and Diaion HP 20 (Mitsubishi); acrylic resins such as XAD7 or XAD8 (Rohm and Haas); polyamides such as polycaprolactames, nylons and cross-linked polyvinylpyrrolidones generally having a pore volume (ml/g) ranging between 1 and 5, surface area ($m^2$/g) ranging between 1 and 100, apparent density (g/ml) ranging between 0.15 and 0.50, average pore diameter (Angstrom units) ranging between 100 and 3000 and particle size distribution where at least 40 percent of the particle size is lower than 300 micrometers, such as Polyamide-CC 6, Polyamide-SC 6, Polyamide-CC 6.6, Polyamide-CC 6AC, and Polyamide-SC 6AC (Macherey-Nagel & Co., West Germany), the polyvinylpyrrolidone resin PVP-CL (Aldrich Chemie GmbH & Co., KG, West Germany); and charcoal. In the case of polystyrene resins, polystyrene-divinylbenzene resins or acrylic resins a preferred eluent is a buffered mixture of water-miscible solvents; in the case of a polyamide resin the eluent is preferably an aqueous mixture of water-miscible solvents, while for charcoal a preferred eluent is a lower ketone such as acetone or a lower alcohol such as methanol.

The term "water-miscible solvent" as used in this application, is intended to have the meaning currently given in the art to this term and refers to solvents that, at the conditions of use, are miscible with water in a reasonably wide concentration range.

Examples of water-miscible organic solvents that can be used in the elution of the antibiotic substances of the invention are: lower alkanols, e.g. ($C_1$–$C_3$)alkanols such as methanol, ethanol, and propanol; phenyl ($C_1$–$C_3$)alkanols such as benzyl alcohol; lower ketones, e.g. ($C_3$–$C_4$)ketones such as acetone and ethylmethylketone; cyclic ethers such as dioxane and tetrahydrofuran; glycols and their products of partial etherification such as ethylene glycol, propylene glycol, and ethylene glycol monomethyl ether; lower amides such as dimethylformamide and diethylformamide; acetic acid, dimethylsulfoxide and acetonitrile.

The further purification of a crude preparation of antibiotic GE1655 complex can be accomplished by any of the known techniques but it is preferably conducted by means of chromatographic procedures.

Examples of these chromatographic procedures are those reported above in relation to the recovery step and include also chromatography on stationary phases such as silica gel, allumina, Florisil, and the like, with an organic eluting phase made of mixtures of solvents including halogenated hydrocarbons, ethers, ketones of the type already mentioned above or reverse phase chromatography on silanized silica gel having various functional derivatizations and eluting with an aqueous mixture of water-miscible solvents of the kind mentioned above.

Conveniently, also the so-called steric exclusion chromatographic technique can be employed with good purification results. In particular, controlled pore cross-linked dextrans in which most hydroxyl groups have been alkylated, e.g. Sephadex LH-20 (Pharmacia Fine Chemicals, Ab), are usefully employed in this technique.

The fractions recovered from the purification step (e.g. exclusion chromatography on Sephadex LH-20) are pooled together, concentrated under reduced pressure, and precipitated by addition of a precipitating agent selected from those mentioned above (e.g. petroleum ether), giving pure antibiotic GE1655 complex.

As usual in this art, the production as well as the recovery and purification steps may be monitored by a variety of analytical procedures including bioassays such as paper disc or agar diffusion assays on sensible microorganisms, e.g. *Candida albicans*, or TLC or HPLC procedures, which may involve a U.V. or microbial detection step.

A preferred HPLC technique is represented by a reverse phase HPLC using a column with porous and spheric particles of silanized silica gel, e.g. silica gel functionalized with C-8 alkyl groups having an uniform diameter (such as 5 micrometer Bakerbond$^R$ Octyl (CS) supplied by J. T. Baker Research Products Phillisburg, N.J. 08865 USA), a pre-column which is a silica gel functionalized with C-8 alkyl groups (such as octasilane silica gel 5 micrometer RP 8 Brownlee Labs.), and an eluent which is a linear gradient mixture of polar water miscible solvents, such as one of those described above, in an aqueous buffered solution. Preferably this solution is adjusted to pH 5–7. A most preferred eluent is represented by a linear gradient from 40 to 60% of eluent B in eluent A (v/v) wherein eluent B is a mixture of acetonitrile/tetrahydrofuran/isopropyl alcohol/aqueous buffer, pH 5–7, 35:25:10:30, and eluent A is a mixture of acetonitrile/aqueous buffer, pH 5–7, 20:80.

The separation of factors A, B, and C may be conveniently carried out by preparative HPLC methods which utilize essentially the same conditions described above for the analytical monitoring.

A preferred preparative HPLC technique is represented by a reverse phase HPLC chromatographic system equipped with a silanized silica gel column functionalized with C-18 alkyl groups having an uniform diameter (such as 5 micrometer Nucleosil C18, 250×40 mm, Stagroma, CH-8304 Wallisellen), and an eluent which is a linear gradient mixture of polar water miscible solvents, such as those described above, in an aqueous buffered solution.

A most preferred eluent is represented by a linear gradient from 5% to 10% of eluent B in eluent A wherein eluent B is a mixture of acetonitrile/tetrahydrofuran/aqueous buffer, pH 6.5, 60:20:20 (v/v) and eluent A is a mixture of acetonitrile/aqueous buffer, pH 6.5, 40:60 (v/v).

The column is connected to a Shimadzu SPD-6 AV U.V. detector at 254 nm.

The fractions of various chromatographic runs with homogeneous antibiotic content are pooled together and concentrated thus obtaining separated residual solutions.

The different residues are lyophilizated to give, respectively, antibiotics GE1655 factor A, GE1655 factor B, and GE1655 factor C.

Since antibiotic GE1655 complex and its factors A, B, and C are amphoteric, containing both basic and acid groups, they are capable of forming salts with suitable acids and bases according to conventional procedures. The pharmaceutically acceptable salts so formed are also part of this invention. "Pharmaceutically acceptable" salts are salts which are useful in the therapy of warm-blooded animals. Representative and suitable salts of the antibiotics of the invention include those acid addition salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, campboric, glutaric, glycolic, phthalic, tartaric, lauric, stearic, salicylic, methanesulfonic, benzenesulfonic, sorbic, picric, benzoic, cinnamic acid, and the like.

Representative examples of these bases are: alkali metal or alkaline-earth metal hydroxides such as sodium, potassium, and calcium hydroxide; ammonia and organic aliphatic, alicyclic or aromatic amines such as methylamine, dimethylamine, trimethylamine, and picoline.

The transformation of the non-salt compounds of the invention into the corresponding addition salts, and the reverse, i.e. the trasformation of an addition salt of a compound of the invention into the non-salt form are within the ordinary technical skill and are encompassed by the present invention.

Physico-chemical characteristics of antibiotic GE1655 complex

A) Ultraviolet absorption spectrum, which is shown in FIG. 1 of the accompanying drawings, and exhibits the following absorption maxima:

|  | Lambda max (nm) |
| --- | --- |
| 0.1 M HCl | 230 (shoulder) |
|  | 240 |
|  | 268 |
| 0.1 M KOH | 240 |
|  | 268 |
| Phosphate buffer | 231 (shoulder) |
| pH 7.4 | 240 |
|  | 268 |
| Methanol | 240 |
|  | 260 (shoulder) |

B) Infrared absorption spectrum in KBr pellet which is shown in FIG. 2 of the accompanying drawings and exhibits the following absorption maxima ($cm^{-1}$): 3398; 2926; 2854; 1705; 1640; 1458; 1419; 1383; 1299; 1279; 1263; 1230; 1141; 1069; 1005; 970; 918; 856; 837; 662; 604; 559

C) $^1$H-NMR spectrum which is shown in FIG. 3 and exhibits the following groups of signals (in ppm) at 500 MHz recorded in DMSO-d$_6$ (hexadeuterodimethylsulfoxide) using TMS as the internal standard (0.00 ppm); the multiplicity of the signals is indicated between parenthesis where:

(s) indicates singlet (d) indicates doublet (m) indicates multiplet (br s) indicates broad singlet 7.55 (br s); 7.16 (m); 6.00–5.75 (m); 5.95–5.80 (m); 5.38 (m); 5.08 (m); 4.68 (m); 4.02 (m); 3.90 (m); 3.83 (m); 3.67 (m); 3.55 (m); 3.09 (m); 3.04 (s); 2.95 (t); 2.73 (s); 2.68 (s); 2.50 (DMSOd$_6$); 2.38 (m); 2.00–1.90 (m) 1.82 (m); 1.74 (m); 1.59 (s); 1.02 (d); 0.93 (d); 0.90–0.75 (d).

D) Positive ion FAB spectrum was obtained on a Kratos MS-50 double focusing mass spectrometer, using 8 kV accelerating voltage.. A saddle field atom gun was used with Xe gas ($2\times10^{-5}$ torr pressure indicated on the source ion gauge) at 6 kV voltage and 1 mA current. The samples were studied in a glycerol matrix acidified with 0.1N CH$_3$COOH in positive ionization mode. FAB-MS analysis shows three protonated molecular ions M+1 at m/z 1082, 1068, and 1054

E) Retention-times (R$_t$) were analyzed by reverse phase HPLC under the following conditions:

column: Bakerbond$^{R*}$ Octyl (C8) (reverse phase silanized silica gel; 5 micrometer) 4.6×250 mm (*) Bakerbond is a trademark of HPLC columns supplied by J. T. Baker Research Products Phillisburg, N.J. 08865 USA precolumn: Brownlee Labs RP 8 (octasilane silica gel; 5 micrometer)

eluent A: CH$_3$CN—6.6 mM ammonium citrate 20:80(v/v)

eluent B: CH$_3$CN—tetrahydrofuran—isopropyl alcohol—6.6 mM ammonium citrate 35:25:10:30(v/v)

elution mode: linear gradient from 40% to 60% of eluent B in eluent A in 20 min.

flow rate: 1.8 ml/min

U.V. detector: 254 nm

Antibiotic GE1655 shows the following R$_t$ values: 10.3, 10.56, 11.12 min.

Physico-chemical characteristics of antibiotic GE1655 factor A

A) Ultraviolet absorption spectrum which exhibits the following absorption maxima:

|  | Lambda max (nm) |
|---|---|
| Phosphate buffer | 240 |
| pH 7.4 | 268 |
| Methanol | 240 |
|  | 260 |

B) $^1$H-NMR spectrum which exhibits the following groups of signals (in ppm) at 500 MHz recorded in DMSO-d$_6$ (hexadeuterodimethylsulfoxide) using TMS as the internal standard (0.00 ppm)): 7.45 (br s); 7.17 (m); 6.30–6.15 (m); 5.95–5.80 (m); 5.39 (m); 5.08 (m); 4.72 (m); 4.02 (m); 3.83 (m); 3.67 (m); 3.3 (H$_2$O); 3.09 (m); 2.73 (s); 2.50 (DMSOd$_6$); 2.38 (m); 2.00–1.90 (m); 1.73 (m); 1.59 (s); 1.02 (d); 0.95 (d); 0.90–0.75 (d)

C) Positive ion FAB spectrum was obtained on a Kratos MS-50 double focusing mass spectrometer, using 8 kV accelerating voltage. A saddle field atom gun was used with Xe gas ($2\times10^{-5}$ torr pressure indicated on the source ion gauge) at 6 kV voltage and 1 mA current. The samples were studied in a glycerol matrix acidified with 0.1N CH$_3$COOH in positive ionization mode. FAB-MS analysis showing the M+H$^+$ peak at m/z 1082

D) Retention-time (R$_t$) was analyzed by reverse phase HPLC under the following conditions:

column: Bakerbond$^{R*}$ Octyl (C8) (reverse phase silanized silica gel; 5 micrometer) 4.6×250 mm (*) Bakerbond is a trademark of HPLC columns supplied by J. T. Baker Research Products Phillisburg, N.J. 08865 USA.

precolumn: Brownlee Labs RP 8 (octasilane silica gel; 5 micrometer)

eluent A: CH$_3$CN—6.6 mM ammonium citrate 20:80(v/v)

eluent B: CH$_3$CN—tetrahydrofuran—isopropyl alcohol—6.6 mM ammonium citrate 35:25:10:30(v/v)

elution mode: linear gradient from 40% to 60% of eluent B in eluent A in 20 min.

flow rate: 1.8 ml/min

U.V. detector: 254 nm

Antibiotic GE1655 factor A shows an R$_t$ value of 11.12 min.

Physico-Chemical characteristics of antibiotic GE1655 factor B:

A) Ultraviolet absorption spectrum, which is shown in FIG. 4 of the accompanying drawings, and exhibits the following absorption maxima:

|  | Lambda max (nm) |
|---|---|
| Phosphate buffer | 240 |
| pH 7.4 | 268 |
| Methanol | 240 |
|  | 260 |

B) $^1$H-NMR spectrum which exhibits the following groups of signals (in ppm) at 500 MHz recorded in DMSO-d$_6$ (hexadeuterodimethylsulfoxide) using TMS as the internal standard (0.00 ppm)): 7.57 (br s); 7.16 (m); 6.30–6.15 (m); 5.95–5.80 (m); 5.39 (m); 5.08 (m); 4.72 (m); 4.02 (m); 3.90 (m) 3.83 (m); 3.67 (m); 3.3 (H$_2$O) 3.06 (m); 2.70 (s); 2.50 (DMSOd$_6$); 2.37 (m); 2.00–1.90 (m); 1.73 (m); 1.59 (s); 1.02 (d); 0.94 (d); 0.90–0.75 (d)

C) Positive ion FAB spectrum was obtained on a Kratos MS-50 double focusing mass spectrometer, using 8 kV accelerating voltage. A saddle field atom gun was used with Xe gas ($2\times10^{-5}$ torr pressure indicated on the source ion gauge) at 6 kV voltage and 1 mA current. The samples were studied in a glycerol matrix acidified with 0.1N CH$_3$COOH in positive ionization mode. FAB-MS analysis shows the M+H$^+$ peak at m/z 1068

D) Retention-time (R$_t$) was analyzed by reverse phase HPLC under the following conditions:

column: Bakerbond$^{R*}$ Octyl (CS) (reverse phase silanized silica gel; 5 micrometer) 4.6×250 mm (*) Bakerbond is a trademark of HPLC columns supplied by J. T. Baker Research Products Phillisburg, N.J. 08865 USA precolumn: Brownlee Labs RP 8 (octasilane silica gel: 5 micrometer)

eluent A: CH$_3$CN—6.6 mM ammonium citrate 20:80(v/v)

eluent B: CH$_3$CN—tetrahydrofuran—isopropyl alcohol—6.6 mM ammonium citrate 35:25:10:30(v/v)

elution mode: linear gradient from 40% to 60% of eluent B in eluent A in 20 min.

flow rate: 1.8 ml/min

U.V. detector: 254 nm

Antibiotic GE1655 factor B shows a $R_t$ value of 10.56 min.

Physico-chemical characteristics of antibiotic GE1655 factor C:

A) Positive ion FAB spectrum was obtained on a Kratos MS-50 double focusing mass spectrometer, using 8 kV accelerating voltage. A saddle field atom gun was used with Xe gas ($2 \times 10^{-5}$ torr pressure indicated on the source ion gauge) at 6 kV voltage and 1 mA current. The samples were studied in a glycerol matrix acidified with 0.1N $CH_3COOH$ in positive ionization mode. FAB-MS analysis shows the $M+H^+$ peak at m/z 1054

B) Retention-time ($R_t$) was analyzed by reverse phase HPLC under the following conditions:

column: Bakerbond$^{R*}$ Octyl ($R_t$) (reverse phase silanized silica gel; 5 micrometer) 4.6×250 mm (*) Bakerbond is a trademark of HPLC columns supplied by J. T. Baker Research Products Phillisburg, N.J. 08865 USA precolumn: Brownlee Labs RP 8 (octasilane silica gel; 5 micrometer)

eluent A: $CH_3CN$—6.6 mM ammonium citrate 20:80(v/v)

eluent B: $CH_3CN$—tetrahydrofuran—isopropyl alcohol—6.6 mM ammonium citrate 35:25:10:30(v/v)

elution mode: linear gradient from 40% to 60% of eluent B in eluent A in 20 min.

flow rate: 1.8 ml/min

U.V. detector: 254 nm

Antibiotic GE1655 factor C shows a $R_t$ value of 10.3 min.

Biological activity of the antibiotic products

The antimicrobial activity of the compounds of the invention can be demonstrated by a series of standard tests in vitro.

Minimal inhibitory concentrations (MIC) are determined by microbroth dilution methodology. Inocula are $10^4$–$10^5$ cfu/ml for yeasts, Aspergillus niger, and bacteria; about 1% of a standardized aqueous (0.2% v/v) Tween 80 suspension containing a mixture of mycelia and conidia for dermatophytes. Fungi are grown at 30° C., MIC are read at 20–24 h for Candid albicans, at 48 h for Cryptococcus neoformans and Aspergillus niger, at 72 h for Trichophyton mentagrophytes and Microsporum canis. Media used are pH 7 phosphate-buffered yeast nitrogen base broth (Difco), supplemented with glucose (1% w/v) and L-asparagine (0.15% w/v) for yeasts and Aspergillus niger, YM broth (Difco) for dermatophytes. Bacteria are cultured at 37° C., MIC are read at 20–4 h except for Neisseria gonorrhoeae, Haemophilus influenzae, Propionibacterium acnes, and Bacteroides fragilis which are read at 48 h. Neisseria gonorrhoeae and Haemophilus influenzae are incubated in a 5% $CO_2$ atmosphere; anaerobes are incubated in an anaerobic gas mixture. Media used are Oxoid Iso-Sensitest broth (staphylococci, Enterococcus faecalis, Escherichia coli, Proteus mirabilis, Pseudomonas aeruginosa), Difco Todd-Hewitt broth (streptococci), Difco GC Base broth with 1% BBL Isovitalex for Neisseria gonorrhoeae, Difco Brain Heart Infusion broth with 1% Difco supplement C for H. influenzae, Oxoid Wilkins-Chalgren broth for anaerobes.

Minimal inhibitory concentrations for Gardnerella vaginalis are determined by agar dilution on Difco Casman medium base with 5% rabbit blood and 0.15% lysed rabbit blood. Inocula are $10^4$–$10^5$ cfu/spot; microorganisms are incubated at 37° C. in an anaerobic gas mixture; MIC are read at 48 h.

The minimal inhibitory concentrations (MIC) in micrograms/ml for some fungi and bacteria are reported in table IV, V, VI, and VII.

TABLE IV

ANTIFUNGAL M.I.C. DETERMINATIONS

| Strain | M.I.C.(micrograms/ml) | | |
|---|---|---|---|
| | GE1655 complex | Factor A | Factor B |
| Candida albicans L145 SKF2270 | 8 | 8 | 16 |
| + 30% bovine serum | 32 | 32 | 64 |
| Candida albicans L115 ATCC 10231 | 8 | 8 | 16 |
| Cryptococcus neoformans L123 SKF1110 | 2 | 2 | 4 |
| Aspergillus niger L 53 ATCC 10535 | 4 | 4 | 16 |
| Trichophyton mentagrophytes L634 SKF17410 | 0.5 | 1 | 2 |
| Microsporum canis L642 IPF | 4 | 4 | 16 |

TABLE V

ANTIBACTERIAL M.I.C. DETERMINATION

| Strain | M.I.C. (mcg/ml) Antibiotic GE1655 complex |
|---|---|
| Staph. aureus L165 Tour | 8 |
| + 30% bovine serum | 64 |
| Staph. epidermidis L147 ATCC 12228 | 4 |
| Staph. haemolyticus L602 | 8 |
| Strep. pyogenes L49 C203 | 8 |
| Strep. pneumoniae L44 UC41 | 8 |
| Strep. faecalis L149 ATCC 7080 | 32 |
| Propionibacterium acnes L1014 ATCC 6919 | 4 |
| Bacteroides fragilis L1010 ATCC 23745 | 8 |
| Neisseria gonorrhoeae L997 ISM68/126 | 32 |
| Haemophilus influenzae L970 type b ATCC 19418 | 16 |
| Escherichia coli L47 SKF12140 | >128 |
| Proteus vulgaris L79 ATCC 881 | >128 |
| Pseudomonas aeruginosa L4 ATCC 10145 | >128 |

TABELLA VI

ACTIVITY OF GE1655 COMPLEX AGAINST CANDIDA SPECIES

| Species | N. strain | mcg/ml | | |
|---|---|---|---|---|
| | | MIC range | $MIC_{50}$ | $MIC_{90}$ |
| C. albicans* | 24 | 2–8 | 4 | 4 |
| C. maris L1660 | 1 | 2 | | |
| C. glabrata L1661 | 1 | 4 | | |
| C. kruzei L244 | 1 | 4 | | |
| C. tropicalis L243 | 1 | 2 | | |

*The test was carried out on a series of 24 Candida albicans strains of the applicant's collection identified with the following internal code numbers: L1404, L1405, L1406, L1407, L1408, L1409, L1410, L1411, L1412, L1413, L1414, L1415, L1416, L1417, L1418, L1429, L1430, L1431, L1432, L1632, L1633, L1662, L1664, L1665.

TABLE VII

ACTIVITY OF GE1655 COMPLEX AGAINST GARDNERELLA VAGINALIS (CLINCAL ISOLATES)

| N. strains | mcg/ml | | |
|---|---|---|---|
| | MIC range | $MIC_{50}$ | $MIC_{90}$ |
| 14* | 32->128 | 64 | 128 |

*The test was carried out on a series of 14 Gardnerella vaginalis strains of the applicant's collection identified with the following internal code numbers: L332, L529, L530, L531, L1622, L1623, L1624, L1625, L1626, L1627, L1628, L1629, L1630, L1631.

Fungicidal activity of GE1655 complex

A logarithmically growing culture of *C. albicans* SKF 2270 in buffered supplemented yeast nitrogen broth (30° C., with agitation) was exposed to concentrations of GE1655 complex above the MIC value and sampled at intervals. The initial inoculum was about $10^6$ cfu/ml. Suitably diluted aliquots were plated in duplicate by inclusion in 2.5 ml of Sabouraud soft agar (0.7%) on Sabouraud agar plates for determination of viable colony forming units (cfu). Plates were incubated for two days at 30° C.

After 48 h at a concentration of GE1655 complex four times the MIC (32 mcg/ml) more than 99.5% of yeasts were killed. More than 99.9% killing was obtained in the first 7 hours with some regrowth between 7 and 24 h.

Ge1655 complex is thus to be considered fungicidal for *C. albicans*.

The antibiotics of the invention are also active against phytopatogenic fungi.

In vivo antifungal activity of GE1655 complex

The in vivo protective activity of the antibiotic GE1655 complex against *Candida albicans* in ovariectomized female CD rats (weighing 150–170 g, obtained from Charles River 7 days after surgery) was determined. *Candida albicans* L145 was grown overnight in Sabouraud dextrose broth (Difco) at 30° C. The culture was centrifuged at 6000 r.p.m. for 20 min at 4° C., the yeast was resuspended in nutrient broth N.2 (Oxoid) containing 15% (v/v) glycerol and stored at −80° C. After 7 days of acclimatization in a temperature and humidity controlled room, the animals received 4 mg of estradiol benzoate (Sigma) subcutaneously. Four days later they were infected by intravaginal (i.va.) instillation with 0.025 ml of thawed *Candida albicans* suspension (about $5 \times 10^6$ cfu/rat).

GE1655 complex and miconazole (Sigma) were dissolved in dimethylsulfoxide (DMSO) and then diluted 1:10 with PEG 400; this risulted in homogeneous suspensions. Animals received 0.1 ml of one of these suspensions i.va. twice daily for three days starting 24 h after the infection. Control animals were treated with the vehicle (10% DMSO in PEG 400).

The presence of Candida was determined by inserting a disposable 0.01 ml calibrated loop into the vagina. The sample was resuspended in 0.2 ml of sterile peptonized saline and cultivated on Sabouraud dextrose agar containing 100 mg/l of rifampicin to inhibit growth of bacterial contaminants.

The results obtained in 2 different *Candida vaginitis* experiments (Table VIII) show that the animals treated daily with 10 mg of GE1655 complex or 4 mg of miconazole had vaginal load significantly lower (p<0.01) than the control group.

TABLE VIII

*CANDIDA VAGINITIS* IN OVARIECTOMIZED RATS.
Data from 2 experiments

| Therapy | Dose mg/rat per treat. | Route | Mean log$_{10}$ cfu ± SD/sample** | |
|---|---|---|---|---|
| | | | exp. 1 | exp. 2 |
| Vehicle* | | i.va. | 3.75 + 0.31 | 3.66 + 0.62 |
| Miconazole | 4 | " | 1.20 + 1.01 | 1.24 + 0.86 |
| GE1655 complex | 10 | " | 1.94 + 0.51 | 1.90 + 0.60 |

*DMSO and PEG 400 (10:90)
**cfu/sample after 3 days of treatment

Acute toxicity data

The acute toxicity of antibiotic GE1655 complex in mice was determined upon intraperitoneal (i.p.), intravenous (i.v.), and oral (p.o.) administration.

Male and female $CD_1$ mice (weight 18–22 g, Charles River) were used. Antibiotic GE1655 was solubilized in DMSO and 5% glucose solution buffered at pH 7 (10:90). The animals were treated with a single dose of 20, 10 or 5 mg/kg i.v.; 40, 20 or 10 mg/kg i.p.; 500 or 250 mg/kg p.o.

The $LD_{50}$ was estimated on the seventh day after treatment by the Spearman and Kaerber method (D. J. Finney "Statistical Methods in Biological Assay" pp. 524–530 Charles Griffin and Co. Ltd. London 1952). The $LD_{50}$'s for the various routes are in table IX. In general, death occurred within a few minutes after treatment; 2/4 animals treated i.p. with 20 mg/kg died on day 2. All the surviving animals showed slight sedation during the first ten hours of observation. Gross necroscopy did not reveal any alterations.

TABLE IX

ANTIBIOTIC GE1655 COMPLEX ACUTE TOXICITY IN THE MOUSE

| | $LD_{50}$ mg/kg | | |
|---|---|---|---|
| Route | i.v. | i.p. | p.o. |
| | 5 | 15 | >500 |

Transcutaneous toxicity

Antibiotic GE1655 complex was solubilized in DMSO and pH 7 buffered methylcellulose (Methocel$^R$, Dow Chemical Co.) (10:90).

$CD_1$ mice (weight 20–22 g, Charles River) of both sexes were used (4 mice per dose level). The animals were anaesthetized with 3 ml/kg of an aqueous solution containing 0.05 mg/ml of fentanyl and 2.5 mg/ml of droperidol (Leptofen$^R$ Carlo Erba) plus 5 mg/kg of chlordiazepoxide (Valium$^R$ Roche) i.p.; the back of each mouse was abraded with emery paper and then treated topically with a single dose of 10 or 5 mg of antibiotic GE1655 complex.

No symptoms of toxicity were observed.

In view of the broad spectrum of activity, the antibiotics of the present invention are adaptable to being utilized in various applications of antifungal compositions. In such use, compounds may be admixed with a biologically inert carrier, optionally with the aid of a surface active dispersing agent, the nature of which would vary depending on whether the use is for the control of pathogens infecting man or animals, or for control of fungi in agriculture such as in soil or plant parts.

A further object of this invention is to provide pharmaceutical dosage forms particularly useful for the topical administration of antibiotic GE1655 complex and its factors in treatment of vaginal infections. According to this invention topical dosage forms are provided including vaginal tablets, pessaries, creams, ointments, gels, suppositories, lotions, foams, powders, suspensions, drug delivery systems and the like which permit delivery and release of the active substance into the infection sites.

The pharmaceutical dosage forms contain antibiotic GE1655 complex or one of its factors and one or more excipients such as, for example: starch, lactose, glucose, talc, cellulose for solid dosage forms; methylcellulose, modified vegetable oils, mineral oils, polyalkylene glycols, fatty acids and alcohols and the like for semi-solid dosage forms; water, alkanols, glycerol, lanolin, polyethylene glycols, mineral oil, pharmaceutical acceptable organic solvents (e.g. DMSO, methyl-decyl-sulfoxide) and the like for liquid or semi-liquid dosage forms. The dosage forms may optionally contain other active ingredients or ingredients which preserve and favour the antimicrobial action of antibiotic GE1655 complex and its factors in the infection sites (e.g. antiseptics, emulsifiers, surfactants, and the like).

Useful indications for the preparation of suitable topical dosage forms can be found in: Remington's Pharmaceutical Sciences, 17th Edition, 1985 (Mack Publishing Company, Easton, Pa.).

The amount of active substance in the finished dosage forms depends on the minimal inhibitory concentration of the antibiotics of the invention against the infection causative agents and their particular type of formulation.

The dosage may obviously be adjusted according to the severity of the infection and the type of patients. Experimental tests for determining the sensitivity of the microorganisms isolated from the patient may also offer useful indications to select the appropriate dosage. In general terms, the effective dosage ranges between 10 and 600 mg, preferably 100 and 400 mg, for each vaginal application one to three times daily. The course of treatment may last from 3 to 10 days or longer, if required.

Liquid or semi-liquid dosage forms such as creams, lotions, ointments, foams, and suspensions, generally contain from 0.05 to 5% by weight of antibiotic.

If necessary, this range may be broadened without any substantial modification of the characteristics of the respective dosage form. Solid intravaginal unit dosages such as vaginal tablets and suppositories can be manufactured in different dosages. For instance, they may contain from 10 to 600 mg of the antibiotics of the invention.

Typical drug delivery systems incorporating the antibiotics of the invention are formulated, for instance, with biodegradble polymers for controlled release such as those described at pages 106–119 of the book: Drug Delivery Systems. Fundamentals and Techniques—Edited by P. Johnson and J. G. Loyd-Jones, 1987, Ellis Horwood Ltd. Chichister, England.

For non-medical application, the products of the present invention, either singly or as mixture may be employed in compositions in an inert carrier which includes finely divided dry or liquid diluents, extenders, fillers, conditioners and excipients, including various clays, diatomaceous aerth, talc, and the like, or water and various organic liquids such as lower alkanols, for example ethanol and isopropanol, or kerosene, toluene, and other petroleum distillate fractions or mixtures thereof.

In practicing the invention, an antifungal amount of the compositions may be applied directly to areas where fungal control is desired.

The following examples further illustrate the invention and have not to be interpreted as limiting it in any way.

EXAMPLES

Example 1

Production of Antibiotic GE1655

A culture of *Streptomyces hygroscopicus* ATCC 55085 is grown on oatmeal agar slant for one week at 28°–30° C. and then used to inoculate a 500 ml Erlenmeyer flask containing 100 ml of seed medium having the following composition:

| Yeast extract | 2 g/l |
| Soybean meal | 8 g/l |
| Dextrose | 20 g/l |
| NaCl | 1 g/l |
| CaCO₃ | 4 g/l |
| Distilled water q.s. | 1000 ml |

(adjusted to pH 7.3 before sterilization)

The inoculated flask is incubated at 28° C. for 60 hours on a rotary shaker (200 rpm) and then transferred into a 10 l jar fermentor containing 4 l of the seed medium. This new culture is grown for 48 hours at 28°–30° C. with stirring (about 900 rpm) and aeration (about one standard liter of air per volume per minute).

The obtained broth is then used to inoculate a 70 l jar fermentor containing 50 l of production medium:

| Starch | 2% |
| Peptone | 0.25% |
| Hydrolyzed casein | 0.25% |
| Yeast extract | 0.3% |
| Beef extract | 0.2% |
| Soybean meal | 0.2% |
| Calcium carbonate | 0.1% |

(brought to pH 7.4 before sterilization)

Fermentation conditions:

| stirring | 500 rpm |
| aereation | 0.5 v/v/min. (volume/volume/minute) |
| temperature | 28° C. | and incubated for about 72 hours.

Antibiotic production is monitored by well-agar assay using *Candida albicans* ATCC 10231 grown in minimum Davis medium. The inhibition zones are evaluated after incubation overnight at 28° C.

Example 2

Recovery of Antibiotic GE1655 Complex

After 72 hours of fermentation the above obtained broth is harvested and filtered in the presence of a filter aid (Hyflo).

Antibiotic GE1655 is recovered from the filtrate.

The filtrate is adjusted at about pH 7 and 1.5 liter of resin S112 (Dow Chemical Co.) are added and stirred for 3 hours. After this time the resin is collected by filtration on a Bukner funnel, washed with 1 liter of water for 2 times. The resin is eluted with 2 liters of a buffer having the following composition:

$NaH_2PO_4$ (sodium dihydrogen phosphate monohydrate) 2.5 g/l Methanol Tetrahydrofuran with a ratio of 1:1:1 (v/v) adjusted at pH 7.5 with NaOH 1N.

The eluate is concentrated under reduced pressure to give an aqueous residue which is extracted, first with 350 ml of ethyl acetate for 2 times and then with 400 ml of n-butanol for 2 times.

The ethyl acetate extract is discarded, the butanolic extract is concentrated under reduced pressure and the crude antibiotic GE1655 complex is precipitated by addition of petroleum ether from the concentrated organic phase.

The precipitated antibiotic is collected by filtration and dried giving 10.9 g of crude antibiotic GE1655 complex.

Example 3

Purification of Antibiotic GE1655 Complex

Part of the crude antibiotic GE1655 complex obtained from the process illustated in the example 2, is purified by chromatography on Sephadex LH 20 (Pharmacia Fine Chemicals, Ab) according to the following procedure: 200 mg are dissolved in methanol and applied to a chromatography column containing 100 g of resin LH 20 prepared in methanol. The column is developed with methanol and 40 fractions of 7 ml each are collected.

Fractions are analized by HPLC and microbiologically against *Candida albicans* and pooled according to their antibiotic content.

The pooled fractions containing pure antibiotic GE1655 complex are concentrated under reduced pressures and precipitated by adding petroleum ether to give 41 mg of antibiotic GE1655 complex.

Example 4

Isolation of Antibiotics GE1655 Factor A, Factor B, and Factor C

Part of the crude GE1655 complex is purified by preparative HPLC according to the following procedure:

A portion of this crude antibiotic (20 mg) is dissolved in acetonitrile/water 1:1 (v/v) and injected into a HPLC chromatographic system equipped with a silanized silica gel column (Nucleosil C18, 5 micrometer, 250×40 mm, Stagroma, CH-8304 Wallisellen). Elution is made with a linear gradient of a mixture of solution A and B from 5% to 10% of B in A, in 23 min. at a flow rate of 20 ml/min. Solution A is a mixture of 9 mM ammonium formiate and acetonitrile 60:40 (v/v), adjusted to pH 6.5. Solution B is a mixture of 9 mM ammonium formiate, acetonitrile and tetrahydrofuran, 20:60:20 (v/v), adjusted at pH 6.5.

The column is connected to a Shimadzu SPD-6 AV U.V. detector at 254 nm.

The fractions of 8 chromatographic runs, having homogeneous antibiotic content, are pooled and concentrated to remove acetonitrile and tetrahydrofuran, thus obtaining separated residual solutions containing, respectively, antibiotic GE1655 factor A, antibiotic GE1655 factor B, and antibiotic GE1655 factor C. The 3 different residues are lyophilized to give 15 mg of antibiotic GE1655 factor A (retention time 11.4 min.), 19 mg of antibiotic GE1655 factor B (retention time 10.5 min.), and 5 mg of antibiotic GE1655 factor C (retention time 10.3 min.).

dotted line indicates the U.V. spectrum of GE1655 complex in a methanol solution indicates the U.V. spectrum of GE1655 complex in HCl 0.1M indicates the U.V. spectrum of GE1655 complex in phosphate buffer pH 7.4 indicates the U.V. spectrum of GE1655 complex in KOH 0.1M.

Figure 2:
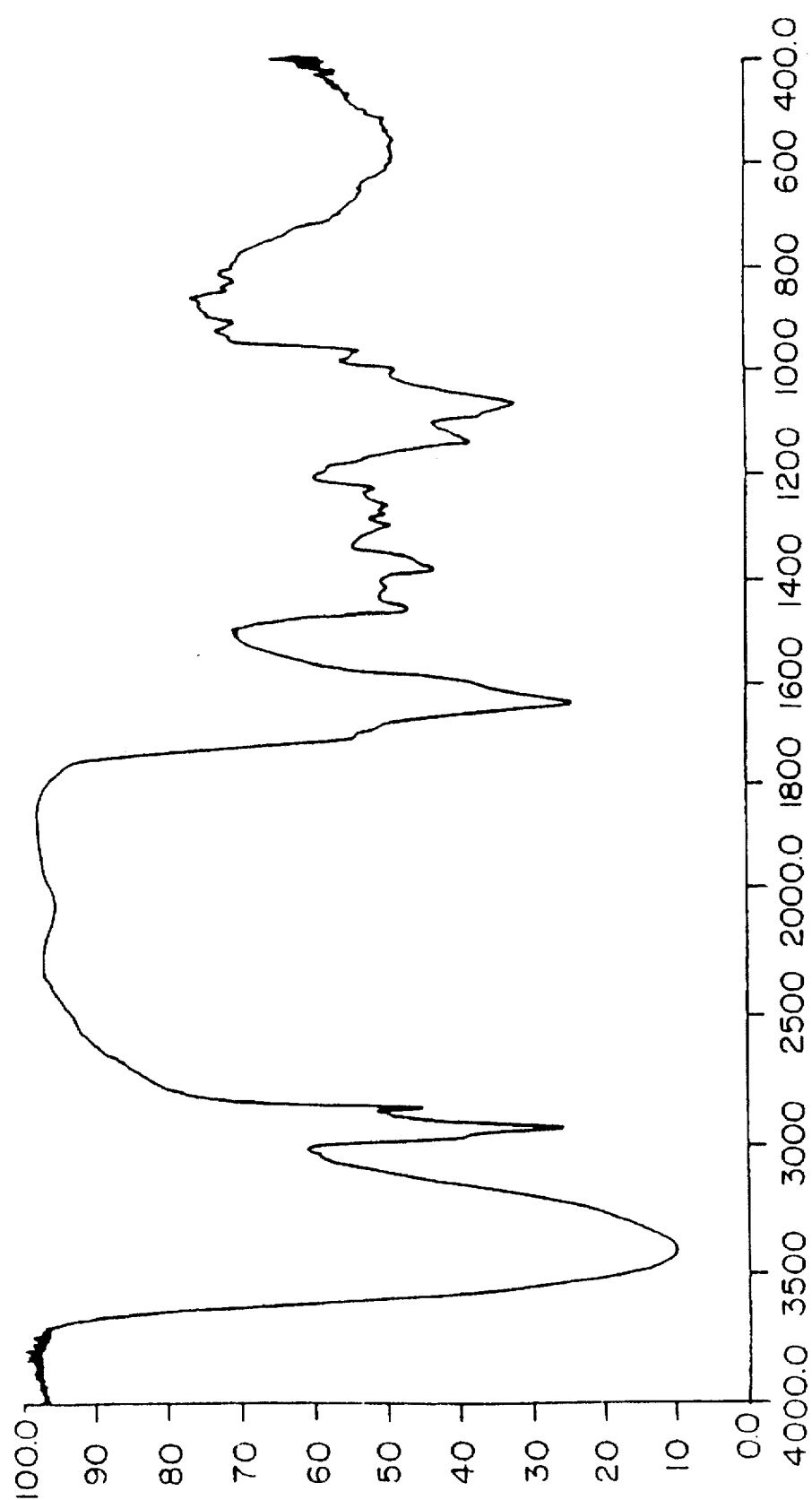

FIG. 2 shows the I.R. spectrum of GE1655 complex in KBR pellet.

Figure 3:
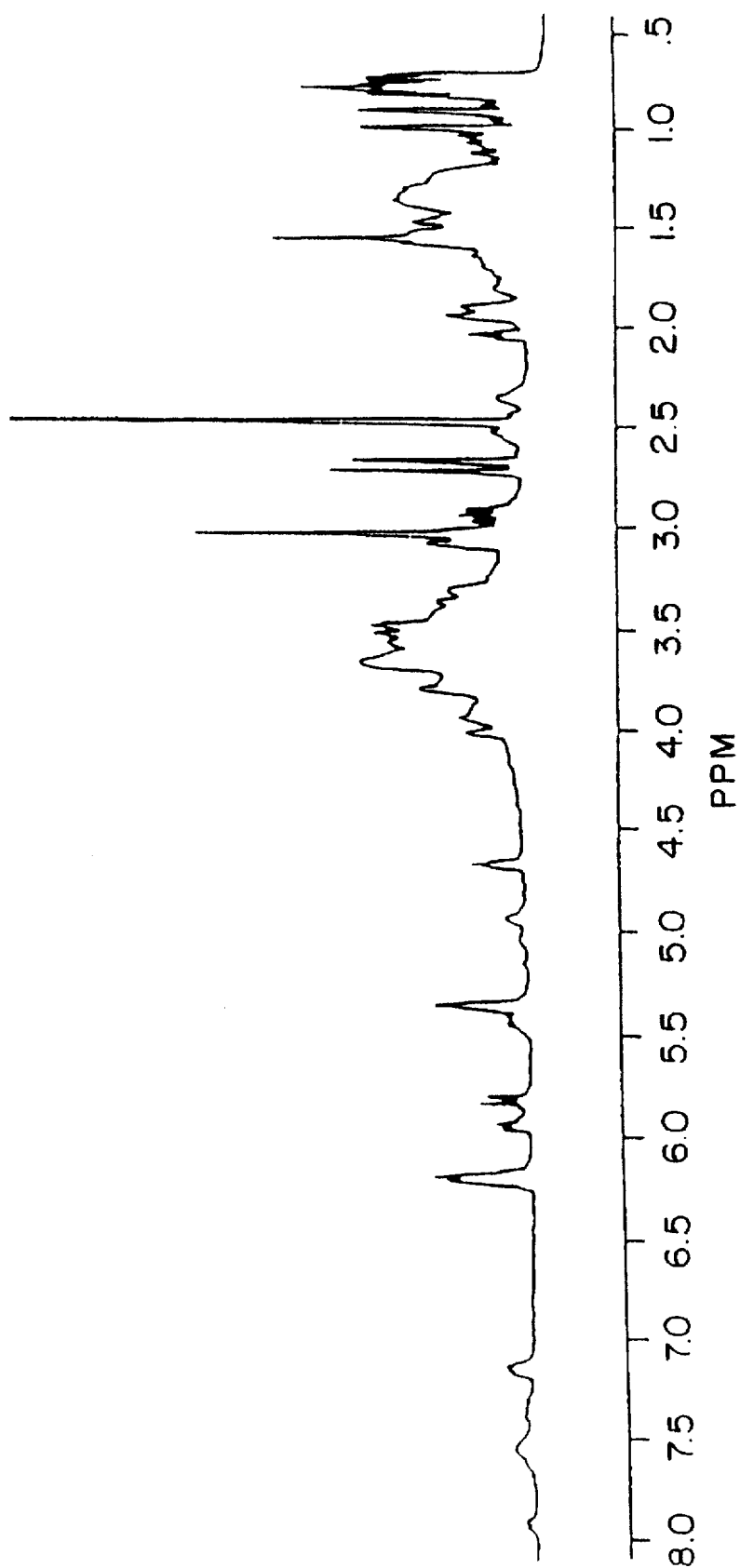

FIG. 3 shows the $^1$H NMR spectrum (500 MHz) of GE1655 complex in DMSO-$d_6$.

Figure 4:
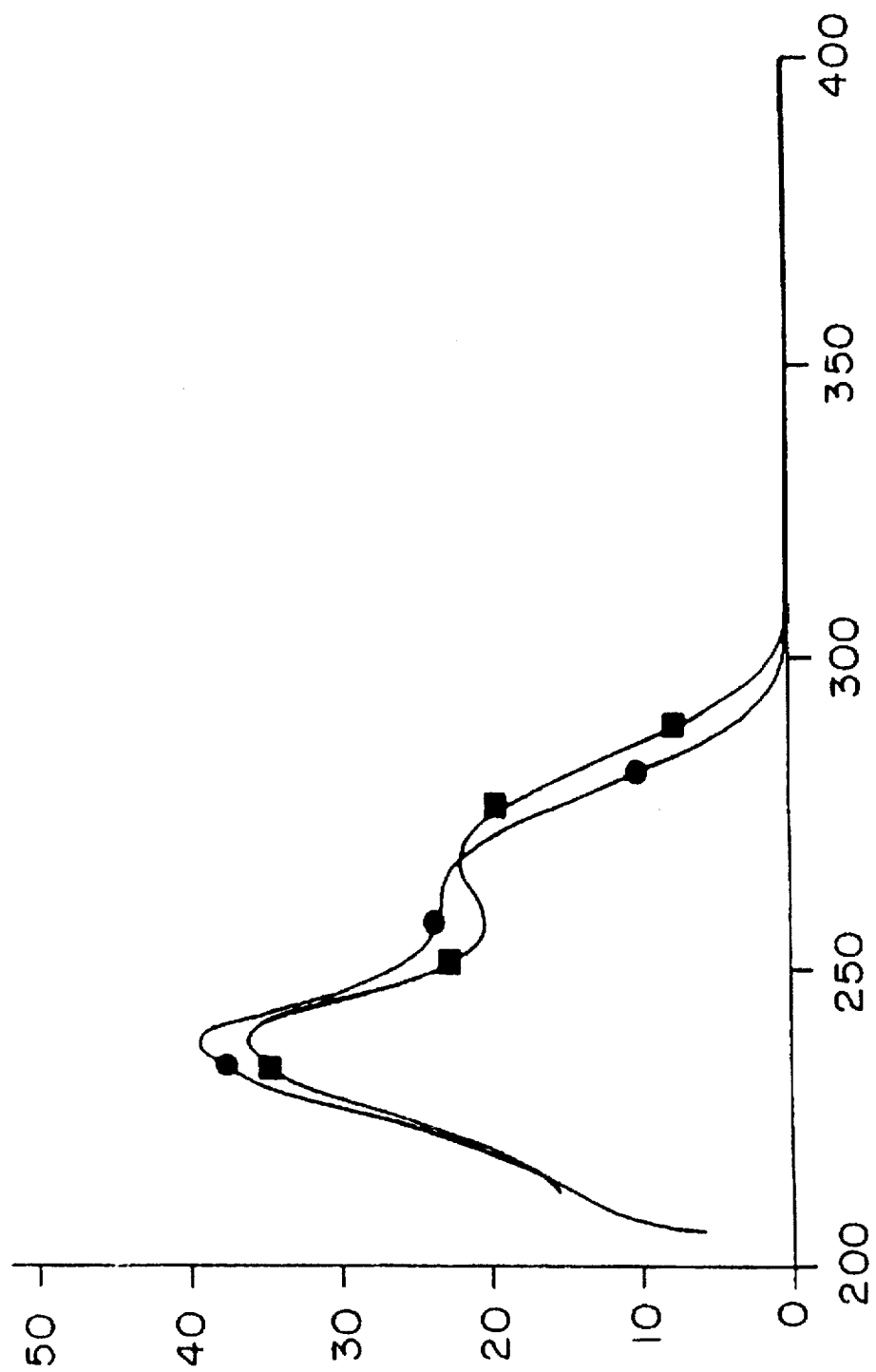

FIG. 4 shows the U.V. spectrum of GE1655 factor B in different solvents:

indicates the U.V. spectrum of GE1655 factor B in a methanol solution indicates the U.V. spectrum of GE1655 factor B in phosphate buffer pH 7.4.

Figure 1:
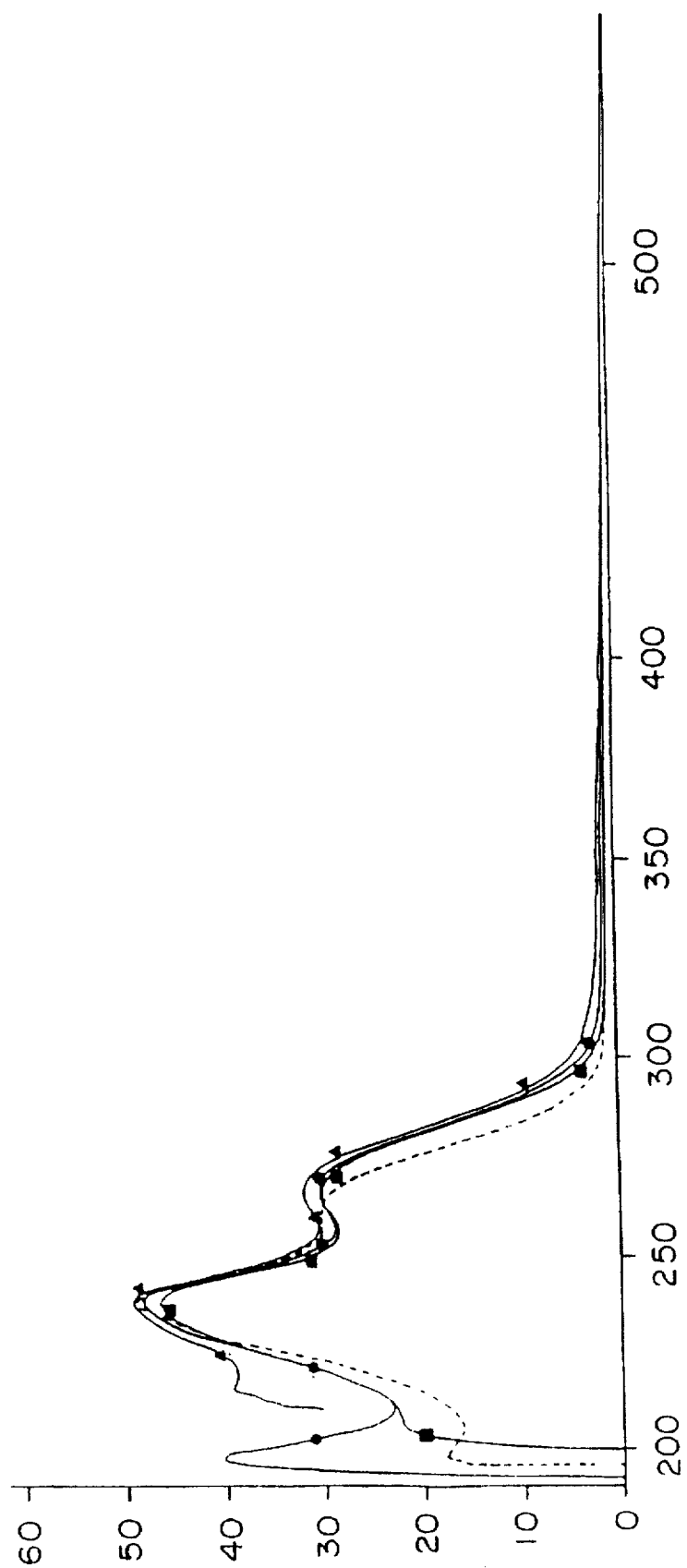
FIG. 1 shows the U.V. spectrum of GE1655 complex in different solvents.

We claim:

1. Antibiotic GE1655 complex having the following characteristics, in the non-salt form:

A) ultraviolet absorption spectrum, which is shown in FIG. 1 of the accompanying drawings, and exhibits the following absorption maxima:

|  | Lambda max (nm) |
| --- | --- |
| 0.1 M HCl | 230 (shoulder) |
|  | 240 |
|  | 268 |
| 0.1 M KOH | 240 |
|  | 268 |
| Phosphate buffer | 235 (shoulder) |
| pH 7.4 | 240 |
|  | 268 |
| Methanol | 240 |
|  | 260 (shoulder) |

B) Infrared absorption spectrum in KBr pellet which is shown in FIG. 2 of the accompanying drawings and exhibits the following absorption maxima (cm$^{-1}$): 3398; 2926; 2854; 1705; 1640; 1458; 1419; 1383; 1299; 1279; 1263; 1230; 1141; 1069; 1005; 970; 918; 856; 837; 662; 604; 559

C) $^1$H-NMR spectrum which is shown in FIG. 3 and exhibits the following groups of signals (in ppm) at 500 MHz recorded in DMSO-$d_6$ (hexadeuterodimethylsulfoxide) using TMS as the internal standard (0.00 ppm): 7.55 (br s); 7.16 (m); 6.00–5.75 (m); 5.95–5.80 (m); 5.38 (m); 5.08 (m); 4.78 (m); 4.02 (m); 3.90 (m); 3.83 (m); 3.67 (m); 3.55 (m); 3.09 (m); 2.95 (t); 2.73 (s); 2.68 (s); 2.5 (DMSO$d_6$); 2.38 (m); 2.00–1.90 (m); 1.82 (m); 1.74 (m); 1.59 (s); 1.02 (d); 0.93 (d); 0.90–0.75 (d)

D) A positive ion FAB spectrum, obtained on a Kratos MS-50 double focusing mass spectrometer, using 8 kV accelerating voltage and a saddle field atom gun with Xe gas (2×10$^{-5}$ torr pressure indicated on the source ion gauge) at 6 kV voltage and 1 mA current in a glycerol matrix acidified with 0.1N CH$_3$COOH in positive ionization mode, showing three protonated molecular ions M+1 at m/z 1082, 1068, and 1054

E) Retention-times ($R_t$) of 10.3, 10.56, 11.12 min. when analyzed by reverse phase HPLC under the following conditions:

column: Bakerbond$^R$ Octyl (C8) (reverse phase silanized silica gel; 5 micrometer) 4.6×250 mm precolumn: Brownlee Labs RP 8 (octasilane silica gel; 5 micrometer)

eluent A: CH$_3$CN—6.6 mM ammonium citrate 20:80 (v/v)

eluent B: CH$_3$CN—tetrahydrofuran—isopropyl alcohol—6.6 mM ammonium citrate 35:25:10:30 (v/v)

elution mode: linear gradient from 40% to 60% of eluent B in elueant A in 20 min flow rate: 1.8 ml/min U.V. detector: 254 nm or its pharmaceutically acceptable salts, which is produced by:

1) fermenting *Streptomyces hygroscopicus* ATCC 55085, under submerged aerobic conditions, with assimilable sources of carbon, nitrogen, and inorganic salts in the fermentation medium, until a sufficient amount of the antibiotic is accumulated therein;

2) recovering said antibiotic GE1655 complex from the fermentation medium, and;
3) purifying said complex.

2. Antibiotic GE1655 factor A having the following characteristics:

A) ultraviolet absorption spectrum which exhibits the following absorption maxima:

|  | Lambda max (nm) |
|---|---|
| Phosphate buffer | 240 |
| pH 7.4 | 268 |
| Methanol | 240 |
|  | 260 |

B) $^1$H-NMR spectrum which exhibits the following groups of signals (in ppm) at 500 MHz recorded in DMSO-$d_6$ (hexadeuterodimethylsulfoxide) using TMS as the internal standard (0.00 ppm)): 7.45 (br s); 7.17 (m); 6.30–6.15 (m); 5.95–5.80 (m); 5.39 (m); 5.08 (m); 4.72 (m); 4.02 (m); 3.83 (m); 3.67 (m); 3.3 ($H_{2O}$); 3.09 (m); 2.73 (s); 2.50 (DMSOd6); 2.38 (m); 2.00–1.90 (m); 1.73 (m); 3.09 (m); 2.73 (s); 2.50 (DMSOd6); 2.38 (m); 2.00–1.90 (m); 1.73 (m); 1.59 (s); 1.02 (d); 0.95 (d); 0.90–0.75 (d)

C) Positive ion FAB spectrum, obtained on a Kratos MS-50 double focusing mass spectrometer, using 8 kV accelerating voltage and a saddle field atom gun with Xe gas ($2\times10^{-5}$ torr pressure indicated on the source ion gauge) at 6 kV voltage and 1 mA current in a glycerol matrix acidified with 0.1N $CH_3COOH$ in positive ionization mode, showing the M+H$^+$ peak at m/z 1082

D) Retention-time ($R_t$) of 11.12 min. when analyzed by reverse phase HPLC under the following conditions:
column: Bakerbond$^R$ Octyl (C8) (reverse phase silanized silica gel; 5 micrometer) 4.6×250 mm
precolumn: Brownlee Labs RP 8 (octasilane silica gel; 5 micrometer)
eluent A: $CH_3CN$—6.6 mN ammonium citrate 20:90 (v/v)
eluent B: $CH_3CN$—tetrahydrofuran—isopropyl alcohol—6.6 mM ammonium citrate 35:25:10:30 (v/v)
elution mode: linear gradient from 40% to 60% of eluent B in eluent A in 20 min.
flow rate: 1.8 ml/min
U.V. detector: 254 nm or its pharmaceutically acceptable salts which is produced by:

1) fermenting *Streptomyces hygroscopicus* ATCC 55085, under submerged aerobic conditions, with assimilable sources of carbon, nitrogen, and inorganic salts in the fermentation medium, until a sufficient amount of the antibiotic is accumulated therein;
2) recovering said antibiotic GE1655 complex from the fermentation medium;
3) purifying said complex, and;
4) isolating said antibiotic GE1655 factor A from said purified complex.

3. Antibiotic GE1655 factor B having the following characteristics:

A) Ultraviolet absorption spectrum, which is shown in FIG. 4 of the accompanying drawings, and exhibits the following absorption maxima:

|  | Lambda max (nm) |
|---|---|
| Phosphate buffer | 240 |
| pH 7.4 | 268 |
| Methanol | 240 |
|  | 260 |

B) $^1$H-NMR spectrum which exhibits the following groups of signals (in ppm) at MHz recorded in DMSO-$d_6$ (hexadeuterodimethylsulfoxide) using TMS as the internal standard (0.00 ppm)): 7.57 (br s); 7.16 (m); 6.30–6.15 (m); 5.95–5.80 (m); 5.39 (m); 5.08 (m); 4.72 (m); 4.02 (m); 3.90 (m) 3.83 (m); 3.67 (m); 3.3 ($H_2O$); 3.06 (M); 2.70 (s); 2.50 (DMSOd$_6$); 2.37 (m); 2.00–1.90 (m); 1.73 (m); 1.59 (s); 1.02 (d); 0.94 (d); 0.90–0.75 (d)

C) Positive ion FAB spectrum, obtained on a Kratos MS-50 double focusing mass spectrometer, using 8 kV accelerating voltage and a saddle field atom gun with Xe gas ($2\times10^{-5}$ torr pressure indicated on the source ion gauge) at 6 kV voltage and 1 mA current in a glycerol matrix acidified with 0.1N $CH_3COOH$ in positive ionization mode FAB-MS analysis showing the M+H$^+$ peak at m/z 1068

D) Retention-time ($R_t$) of 10.56 min when analyzed by reverse phase HPLC under the following conditions:
column: Bakerbond$^R$ Octyl (C8) (reverse phase silanized silica gel; 5 micrometer) 4.6×250 mm
precolumn: Brownlee Labs RP 8 (octasilane silica gel; 5 micrometer)
eluent A: $CH_3CN$—6.6 mM ammonium citrate 20:80 (v/v)
eluent B: $CH_3CN$—tetrahydrofuran—isopropyl alcohol—6.6 mM ammonium citrate 35:25:10:30 (v/v)
elution mode: linear gradient from 40% to 60% of eluent B in eluent A in 20 min
flow rate: 1.8 ml/min
U.V. detector: 254 nm or its pharmaceutically acceptable salts, which is produced by:

1) fermenting *Streptomyces hygroscopicus* ATCC 55085, under submerged aerobic conditions, with assimilable sources of carbon, nitrogen, and inorganic salts in the fermentation medium, until a sufficient amount of the antibiotic is accumulated therein;
2) recovering said antibiotic GE1655 complex from the fermentation medium;
3) purifying said complex, and;
4) isolating said antibiotic GE1655 factor B from said purified complex.

4. Antibiotic GE1655 factor C having the following characteristics:

A) Positive ion FAB spectrum, obtained on a Kratos MS-50 double focusing mass spectrometer, using 8 kV accelerating voltage and a saddle field atom gun with Xe gas ($2\times10^{-5}$ torr pressure indicated on the source ion gauge) at 6 kV voltage and 1 mA current in a glycerol matrix acidified with 0.1N $CH_3COOH$ in positive ionization mode showing the M+H$^+$ peak at m/z 1054

B) Retention-time (R$^t$) of 10.3 min when analyzed by reverse phase HPLC under the following conditions:
column: Bakerbond$^R$ Octyl (C8) (reverse phase silanized silica gel; 5 micrometer) 4.6×250 mm precolumn: Brownlee Labs RP 8 (octasilane silica gel; 5 micrometer)

eluent A: $CH_3CN$—6.6 mM ammonium citrate 20:80 (v/v)

eluent B: $CH_3CN$—tetrahydrofuran—isopropyl alcohol—6.6 mM ammonium citrate 35:25:10:30 (v/v)

elution mode: linear gradient from 40% to 60% of eluent B in eluent A in 20 min flow rate: 1.8 ml/min U.V. detector: 254 nm or its pharmaceutically acceptable salts, which is produced by:

1) fermenting *Streptomyces hygroscopicus* ATCC 55085, under sumberged aerobic conditions with assimilable sources of carbon, nitrogen, and inorganic salts in the fermentation medium, until a sufficient amount of the antibiotic is accumulated therein;

2) recovering said antibiotic GE1655 complex from the fermentation medium;

3) purifying said complex, and;

4) isolating said antibiotic GE1655 factor C from said purified complex.

5. A pharmaceutical composition which contains a compound of any one of claims 1, 2, 3 or 4 which is present in an effective amount in admixture with a pharmaceutically acceptable carrier.

6. A method for the treatment of fugal infections comprising the administration of an effective amount of a compound according to any one of claims 1, 2, 3, or 4 to a patient in need thereof.

7. A method according to claim 1 in which said fungus is *candida albicans*.

* * * * *

UNITED STATES PATENT AND TRADEMARK OFFICE
CERTIFICATE OF CORRECTION

PATENT NO. : 5,674,490

DATED : October 7, 1997

INVENTOR(S) : Franco Maria Spreafico; Ernesto Riva; Graziella Beretta; Khalid Islan; Maurizio Denaro It is certified that error appears in the above-identified patent and that said Letters Patent is hereby corrected as shown below:

Column 19, Line 41 of Patent states "20:90" and should read --20:80--.

Signed and Sealed this

Twelfth Day of May, 1998

*Attest:*

BRUCE LEHMAN

*Attesting Officer*     *Commissioner of Patents and Trademarks*